United States Patent
Kametani et al.

[11] Patent Number: 4,939,247
[45] Date of Patent: Jul. 3, 1990

[54] GAMMA-LACTONE DERIVATIVES AND PROCESS OF PREPARING SAME

[75] Inventors: Tetsuji Kametani, Tokyo; Toshio Honda, Yokohama, both of Japan

[73] Assignee: Itaro Horiuchi & Co., Ltd., Japan

[21] Appl. No.: 370,920

[22] Filed: Jun. 23, 1989

Related U.S. Application Data

[62] Division of Ser. No. 34,734, Apr. 6, 1987, Pat. No. 4,874,551.

[51] Int. Cl.$^5$ .................. C01J 19/00; C01J 21/00; C01J 53/00; C01J 63/00
[52] U.S. Cl. .................................................. 540/16
[58] Field of Search .................................... 540/16

[56] References Cited
PUBLICATIONS
Kametani I, Chem Abs 105, 191498 (1986).
Kametani II, Chem Abs 107, 154592.

*Primary Examiner*—Mark L. Berch
*Attorney, Agent, or Firm*—Oldham & Oldham

[57] ABSTRACT

Gamma-lactone derivatives represented by the formula (I)

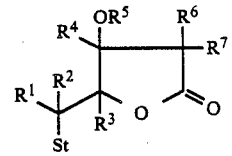

wherein when $R^1$ is methyl group, $R^2$ is hydrogen, hydroxyl group or trifluoroacetoxyl group and $R^2$ may combine with $R^3$ to form a pi bond; when $R^1$ combines with $R^2$ to form methylene group, $R^3$ is hydrogen; $R^4$ and $R^6$ are hydrogen, respectively, or may combine to form a pi bond; $R^5$ is hydrogen or a protecting group for hydroxyl group; $R^7$ is hydrogen or straight-chain or branched alkyl group; and St is a steroid nucleus represented by the following formula (B):

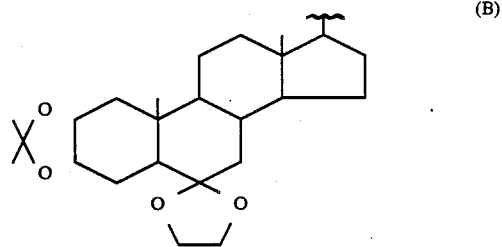

According to the process of the present invention, the introduction of carbon chains which form polyhydroxylated steroid side chains of brassinolides or the like into steroid nucleus is carried out in one-step with the control of stereochemistry of the contiguous four acyclic chiral centers.

4 Claims, No Drawings

GAMMA-LACTONE DERIVATIVES AND PROCESS OF PREPARING SAME

This is a divisional of co-pending application Ser. No. 07/034,734 filed on Apr. 6, 1987 now U.S. Pat. No. 4,874,551.

Background of the Invention

1. Technical Field of the Invention

The present invention relates to γ-lactone derivatives and a process of preparing the γ-lactone derivatives. In particular, the present invention relates to γ-lactone derivatives which are useful as a starting material for synthesis of brassinolide, epibrassinolide and bisnorbrassinolide and derivatives thereof, and also a process of preparing the same.

2. Description of the Prior Art

Recently, the study of the synthesis of brassinolide which has the plant growth promoting activity and brassinosteroids which are analogues of brassinolide has been actively carried out in the hope of producing the brassinolide and derivatives thereof with high stereoselectivity.

Many methods for synthesis of brassinosteroids have been reported to date, and in most of which utilize pregnane-20-carboxaldehyde as a starting material, and comprise a step of introducing carbon chain into such starting material. Accordingly, in adopting such conventional methods, the following defects were found: The by-production of stereoisomer is inevitable; On subsequent introduction of oxygen-functional group, reduction, introduction of alkyl group, special reactant and expensive reagents must be used.

As a typical example of such method, it was disclosed in J. Chem. Soc. Perkin I, 1983, 383. As disclosed in the literature, the method is carried out in the accordance with the reaction process described below; The carbon chain is introduced into pregnane-20-carboxaldehyde (a) by means of a special Grignard reregent (b).

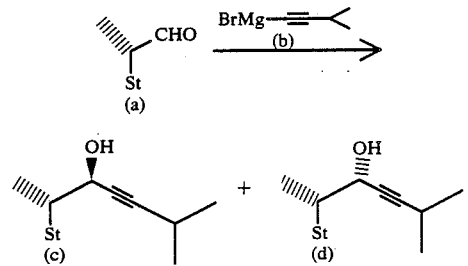

In this method, the product is obtained in the form of mixture of stereoisomers (c) and (d) (3:2) and accordingly the stereoselectivity is low and the resolution of the mixture is complicated.

In addition, the method disclosed in J. Ame. Chem. Soc. 102, 6580 (1980) is accomplished through the following reaction process.

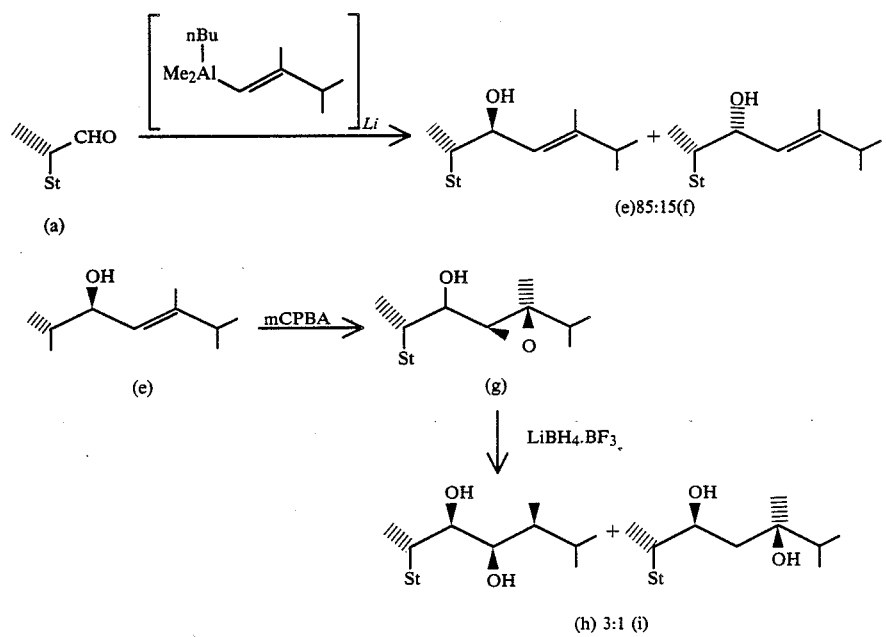

According to this method, unnecessary isomer (i) is by-produced in the reduction of compound (g) with $LiBH_4 \cdot BF_3$.

Summary of the Invention

As mentioned above, in the conventional method, the introduction of carbon chain and the control of configuration are carried out step-by-step.

On the contrary, the inventors found that it is possible to introduce all of necessary carbon chain in one step, and additionally the control of configuration is also conduced by one step.

According to the invention, it is possible to produce easily brassinolide, epibrassinolide and bisnorbrassinolide and derivatives thereof by using a steroid derivative represented by the general formula (II)

and a tetronic acid derivative represented by the general formula (III)

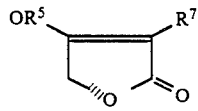

as starting materials. The synthesis of brassinolide or epibrassinolide, or derivatives thereof starts by a reaction of these starting materials and progresses through novel intermediates, the synthesis is accomplished by a reduction thereafter.

The subject matter of the present invention resides, accordingly, in γ-lactone derivatives represented by the general formula (I) described below, which are the novel intermediates mentioned above;

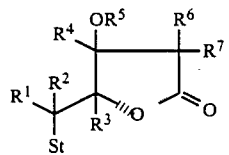

wherein when $R^1$ is methyl group, $R^2$ is hydrogen, hydroxyl group or trifluoroacetoxyl group and $R^2$ may combine with $R^3$ to form π bond; when $R^1$ combines with $R^2$ to form methylene group, $R^3$ is hydrogen; $R^4$ and $R^6$ are hydrogen, respectively, or may combine to form π bond; $R^5$ is hydrogen or a protecting group for hydroxyl group, $R^7$ is hydrogen or straight-chain or branched alkyl group, and St is a steroid nucleus represented by the following formula (A) or (B).

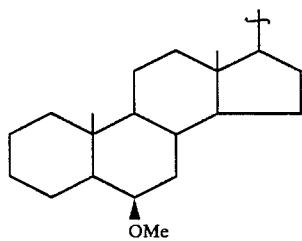

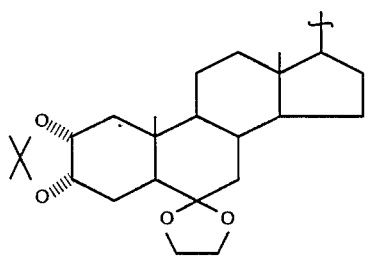

The subject matter of the present invention resides in the process for production of γ-lactone derivatives mentioned above.

The compound of the present invention can be produced by reacting the steroid derivative represented by the general formula (II) [compound (1)] with the tetronic acid derivative represented by the general formula (III) [compound (2)].

The reaction is carried out in the presence of a base. A strong base such as Li-diisopropylamide, Li-cyclohexylisopropylamide, K-t-butoxide, etc. can be used as the base; among them, Li-diisopropylamide is preferable. The reaction is carried out in a solvent selected from inert compound, such as tetrahydrofuran, ether, dioxane, etc. In general, the reaction temperature ranges from −100° C. to +50° C., preferably from −78° C. to 0° C.

Then, the obtained compound (3) represented by the general formula (IV)

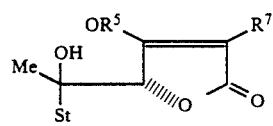

is subjected to dehydration.

The dehydration is carried out by dissolving the compound (3) in pyridine and dropping of SOCl$_2$ thereinto while cooling with ice. As an alternative method, POCl$_3$ can be added dropwise to the solution in pyridine.

The compound (4) represented by the general formula (V)

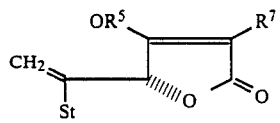

which is obtained after the dehydration is reduced lastly.

The reduction can be carried out in accordance with any method which is usually adopted for the purpose of the reduction of C—C double bond.

In this way, the compound (6) represented by the general formula (VII) can be produced.

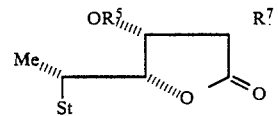

According to another method, the compound (6) can be produced by removing tertiary hydroxyl group of the compound (3) after transforming the compound (3) to trifluoroacetate and then reducing compound (5) represented by the general formula (VI) obtained thereby.

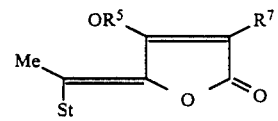

On removing of tertiary hydroxyl group, trifluoroacetate of the compound (3) is heated in benzene together with 1,8-diazabicyclo [5,4,0] undeca-7-ene (DBU) while refluxing. If the conditions of reduction of compound (4) or compound (5) are selected appropriately, the compound (9) represented by the general formula (X)

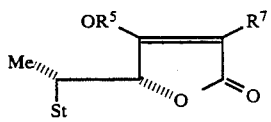

in which only a part of double bonds has been reduced can be obtained. This compound can be isolated. By reducing the obtained compound further, the compound (6) mentioned above can be produced.

· The ergostane derivative (for example, St=steroid nucleus of type A) represented by the general formula (VII) produced by the above processes can easily be transformed into brassinolide derivative by a subsequent reduction disclosed in the reaction process of:

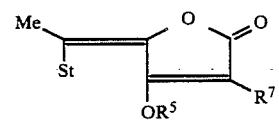

and then a reduction of the compound (7).

The isomerization of compound (4) into compound (7) can be carried out in accordance with the well known isomerization method. For example, the isomerization is accomplished by heating the compound (5) in the presence of DBU while refluxing.

The reduction of the compound (7) into the compound (8) can be conducted with a conventional reduction catalyst such as, for example, Rh-Al$_2$O$_3$, Pt, Pd,

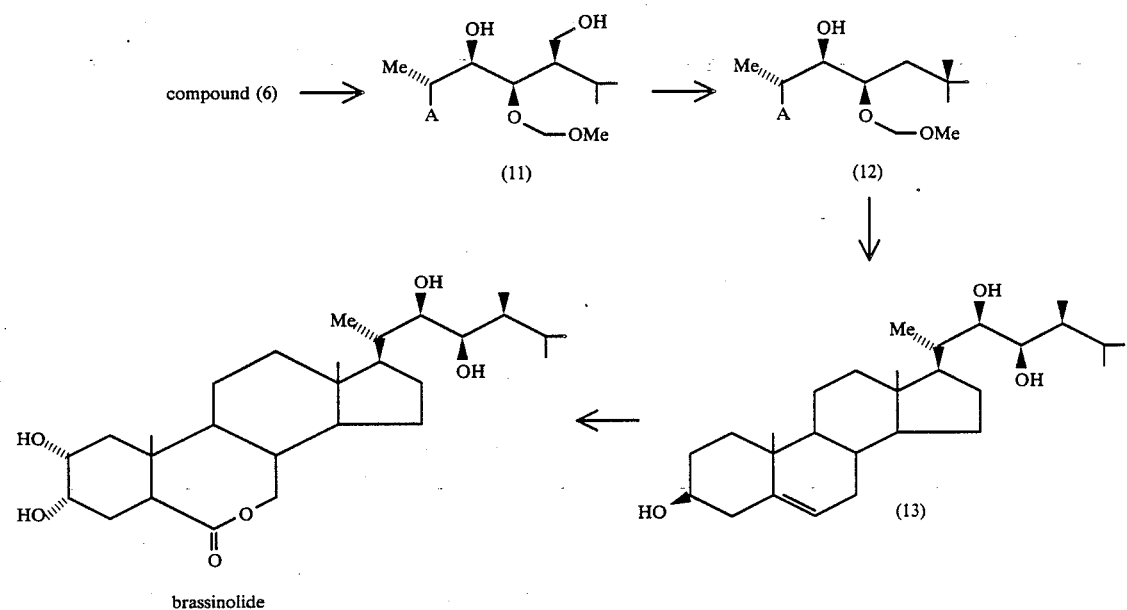

The transformation of the compound (13) into brassinolide can be carried out in accordance with the well known method (J. Ame. Chem. Soc. 102, 6580 (1980)).

Now, according to another aspect of the present invention, a compound (8) represented by the general formula (IX)

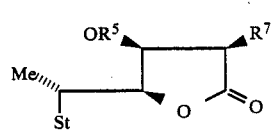

which is an intermediate useful for the synthesis of 22,23,24-epibrassinolide that is a stereoisomer of brassinolide, can be produced by an isomerization of the compound (4) mentioned above into a compound (7) represented by the general formula (VIII)

etc., as similar to the reduction of the compound (4) into the compound (6). By selecting the proper reaction condition during the time of reducing the compound (7), it is possible to stop the reduction in the middle, and to produce and isolate a compound (10) represented by the general formula (XI) in which only a double bond in side chain of lactone ring has selectively been reduced.

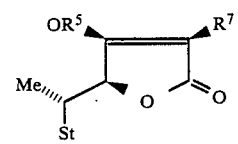

The compound (10) is reduced further to produce the compound (8) mentioned above.

The transformation of the compound (8) [St=steroid nucleus of type (A)] into 22,23,24-epibrassinolide derivative is accomplished by the reduction and the like shown by the reaction process described below. The procedures are same with those of the transformation of the compound (6) into brassinolide.

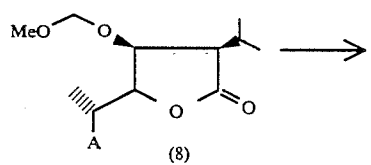
(8)
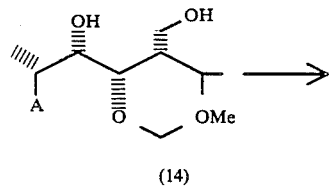
(14)
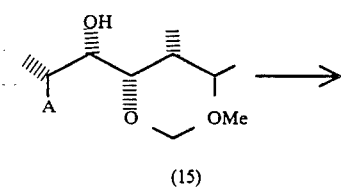
(15)
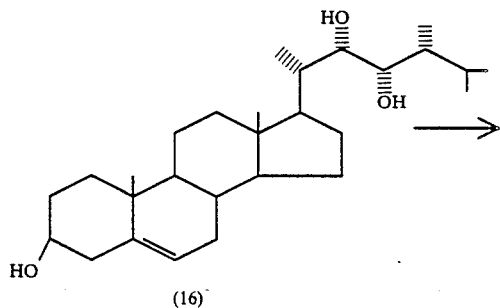
(16)
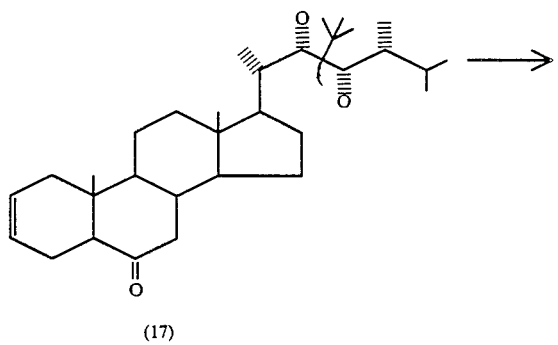
(17)
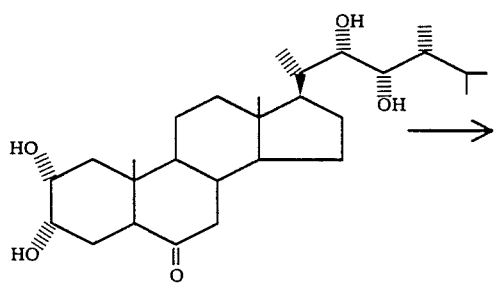
(18)

-continued

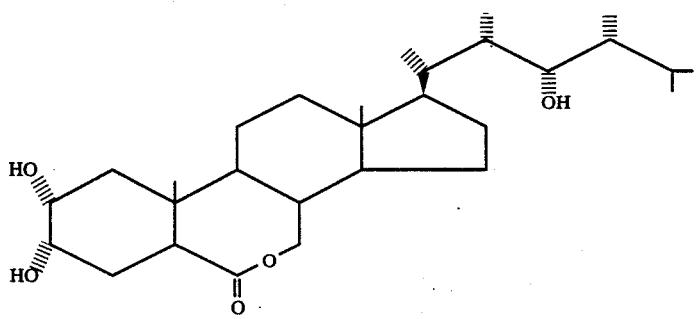

22,23,24-epibrassinolide

The preparation of tetronic acid derivative among raw materials usable in the present invention is carried out as follows:

Reference 1

Synthesis of 3-isopropyltetronic acid 100 ml of solution containing $Br_2$ 107 g in $CHCl_3$ was added to 350 ml of solution containing ethyl-α-isopropyl acetoacetate 105 g in $CHCl_3$ while cooling with ice and stirring. After stirring the mixture for 1 hour at room temperature, the solvent was distilled. The residue was heated at 130° C. for 2 hours. After cooling, 150 ml of hot 10% $K_2CO_3$ solution was added to the reaction mixture. The reaction mixture was washed with $CH_2Cl_2$ and then was acidified with 10% HCl. The reaction mixture was extracted with $CHCl_3$ and the extract liquid was washed with saturated NaCl solution and the solvent was distilled after drying with $Na_2SO_4$. The residue was recrystallized from benzene. In this way, 3-isopropyltetronic acid was obtained as colorless needle-like crystal having the mp of 120°–130° C.

IR $\nu_{max}^{CHCl_3}$ $(cm^{-1})$: 3300, 1740, 1680, 1660

NMR $(CDCl_3)$ δ: 1.22 (6H, d, J=7 Hz, 2×Me); 2.50–3.10 (1H, m, CH); 4.70 (2H, s, $CH_2$)

MS m/z: 142 (M+)

Elemental Analysis: Calc. C 59.14; H 7.0; Found C 59.13; H 7.14.

To further illustrate the present invention, but not limited thereby, the following examples are given. These examples relate to the preparation of compounds having steroid nucleus of A type as St of the general formual (I) mentioned above. The reaction process accomplished in the examples is as follows:

reaction process
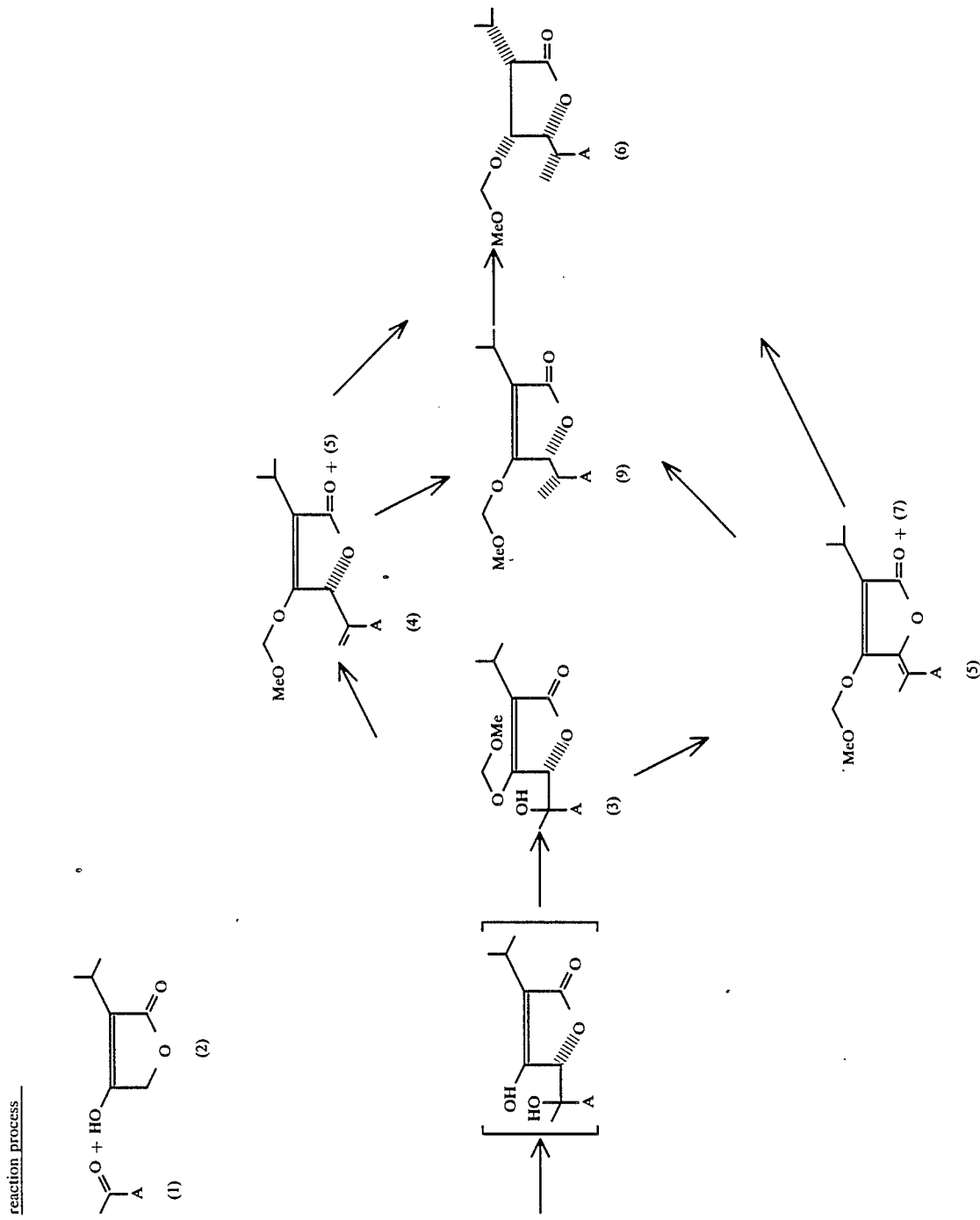

-continued
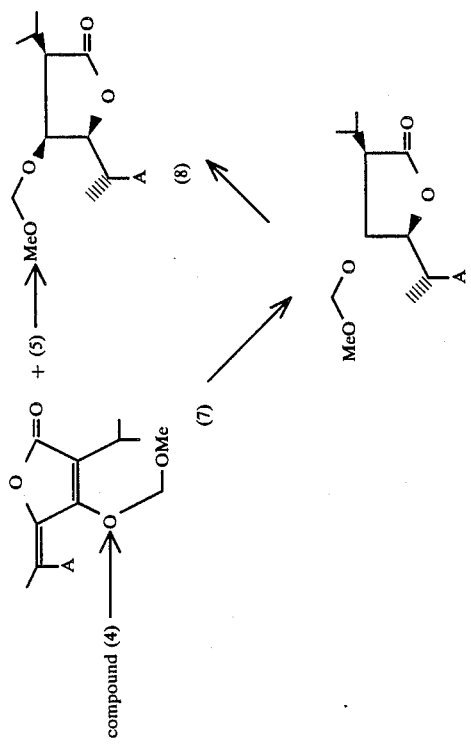

EXAMPLE 1

Synthesis of (22R)-20-hydroxy-6β-methoxy-23-methoxymethoxy-3α,5-cyclo-5α-ergost-23-eno-28,22-lactone [compound (3)]

To 200 ml of anhydrous THF solution containing 2,4-dilithiooxy-3-isopropylfuran, prepared from 3-isopropyltetronic acid obtained in the above Reference 1 and lithium diisopropylamide, 100 ml of solution of 6β-methoxy-3α,5-cyclo-pregna-20-one (1) (5 g) in anhydrous THF was added dropwise at −78° C. The reaction mixture was stirred at −78° C. for 1 hour. After 50 ml of saturated NH$_4$Cl aq. solution was added thereto, the reaction liquid was extracted with AcOEt. The obtained extract was washed with saturated NaCl solution, dried with Na$_2$SO$_4$ and then the solvent was distilled. The residue was dissolved into DMF (100 ml), and K$_2$CO$_3$ 4.7 g was added to the solution and after stirring at 100° C. for 2 hours, 2 ml of chloromethylmethyl ether was added thereto and then the mixture was stirred at 50° C. for further 10 min. After adding AcOEt to the reaction liquid, the reaction liquid was washed with saturated NaCl solution and, after drying with Na$_2$SO$_4$, the solvent was distilled. The residue was chromatographed with silica gel column and the obtained crystals were recrystallized from MeOH, whereby 6.7 g of (yield 85.2%) compound (3) was obtained as colorless prism crystal having the mp of 153°–156° C.

Optical rotation:

$[\alpha]_D$+28.9° (c=1.24, CHCl$_3$)

IR$\nu_{max}^{CHCl_3}$ (cm$^{-1}$): 1750, 1660

NMR (CDCl$_3$) δ: 0.93 (3H, s, CH$_3$) 1.01 (3H, s, CH$_3$); 1.20 (3H, s, CH$_3$); 1.23 (6H, d, J=7 Hz, 2×CH$_3$); 2.76 (1H, t, J=2.5 Hz, CH); 2.70–3.04 (1H, m, CH); 3.32 (3H, s, OCH$_3$); 3.52 (3H, s, OCH$_3$); 4.66 (1H, s, CH); 5.03 and 5.46 (each 1H, each d, J=6 Hz, OCH$_2$).

MS m/z: 516 (M+)

Elemental analysis: Calc. C 72.06; H 0.36; Found C 72.36; H 9.56.

EXAMPLE 2

Synthesis of (22R)-6β-methoxy-23-methoxymethoxy-3α,5-cyclo-5α-ergost-20,(21),23-dieno-28,22-lactone [compound (4)]

10 g of compound (3) prepared in the Example 1 mentioned above was dissolved into pyridine (150 ml) and 7.1 ml of SOCl$_2$ was added dropwise thereto while cooling with ice and, then the obtained solution was stirred at 0° C. for 10 min. The reaction liquid was poured into ice water and the mixture was extracted with Et$_2$O. The extract was washed with water and the solvent was distilled after drying with Na$_2$SO$_4$. The residue was comprised 7.3 g of the desired compound (4) and 720 mg of compound (5) to be mentioned hereafter. The compound (4) was isolated from the residue by chromatography with silica gel column (yield 76%).

mp 166°–167.5° C.

$[\alpha]_D$+92.6° (c=1.59, CHCl$_3$)

IR$\nu_{max}^{CHCl_3}$ (cm$^{-1}$): 1740, 1660

NMR (CDCl$_3$) δ: 0.71 (3H, s, CH$_3$); 1.02 (3H, s, CH$_3$); 1.22 (3H, d, J=7 Hz, CH$_3$); 1.24 (3H, d, J=7 Hz, CH$_3$); 2.76 (1H, t, J=2.5 Hz, CH); 3.33 (3H, s, OCH$_3$); 3.47 (3H, s, OCH$_3$); 4.86 and 5.22 (each 1H, each d, J=4 Hz, OCH$_2$O); 5.17, 5.26 and 5.28 (each 1H, each s, =CH$_2$ and CH).

MS m/z: 498 (M+)

Elemental analysis: Calc. C 74.66; H 9.30; Found C 74.43; H 9.55.

EXAMPLE 3

Synthesis of (22R,23R,24S)-6β-methoxy-23-methoxymethoxy-3α,5-cyclo-5α-ergostano-28,22-lactone [compound (6)]

200 mg of 5% Rh-Al$_2$O$_3$ was added to the 150 ml of AcOEt solution containing 1 g of the compound (4) prepared in the Example 2, and the mixture was shaken for 13 hours under hydrogen atmosphere (7 atm.). After filtration, the solvent was distilled from the reaction liquid. The obtained crude crystals were recrystallized from MeOH, and as a result thereof 910 mg (yield 91%) of the compound (6) was obtained as colorless needle-like crystal having the mp of 133.5°–135° C.

$[\alpha]_D$+67.1° (c=1.46, CHCl$_3$)

IR$\nu_{max}^{CHCl_3}$ (cm$^{-1}$): 1770

NMR (CDCl$_3$) δ: 0.76 (3H, s, CH$_3$); 1.02 (3H, s, CH$_3$); 1.08 (3H, d, J=7 Hz, CH$_3$); 1.15 (3H, d, J=7 Hz, CH$_3$); 1.25 (3H, d, J=7 Hz, CH$_3$); 2.29 (1H, dd, J=8.5 Hz, CH); 2.78 (1H, t, J=2.5 Hz, CH); 3.33 (3H, s, OCH$_3$); 3.41 (3H, s, OCH$_3$); 4.23 (1H, dd, J=3.5 Hz, 1.5 Hz, CH); 4.33 (1H, d d, J=5 Hz, 3.5 Hz, CH); 4.68 and 4.74 (each 1H, each d, J=6 Hz, OCH$_2$O).

MS m/z: 502 (M+)

Elemental analysis: Calc. C 74.06; H 10.03; Found C 74.30; H 10.40.

EXAMPLE 4

Synthesis of (20Z)-6β-methoxy-23-methoxymethoxy-3α,5-cyclo-5α-ergost-20(22),23-dieno-28,22-lactone [compound (5)]

The compound (5) was synthesized from the compound (3) by a method different from that of the Example 2 mentioned above.

5 g of the compound (3) prepared in the Example 1 mentioned above, 4.1 ml of Et$_3$N and 440 mg of 4-pyrrolidinopyridine (PPY) were dissolved into 50 ml of CH$_2$Cl$_2$ and 4.2 ml of (CF$_3$CO)$_2$O was added dropwise thereto. The obtained mixture was stirred at room temperature for 1 hour. Water was then added to the reaction liquid, and the mixture was extracted with AcOEt. The obtained extract was washed with water, and after drying with Na$_2$SO$_4$, the solvent was distilled. The residue was dissolved into 80 ml of benzene and, then 1.4 ml of DBU was added thereto. The mixture was heated while refluxing for 20 min. The reaction liquid was washed with aq. solution of KHSO$_4$ and with saturated NaCl solution, and after drying with Na$_2$SO$_4$, the solvent was distilled.

In this way, 2.9 g of the desired compound (5) was obtained as a mixture with 630 mg of compound (7) which is a stereoisomer (yield 68%) to be mentioned hereafter. The compound (5) was isolated from the mixture by chromatography with silica gel column.

mp 171°–172° C.

$[\alpha]_D$−126.8° (c=1.34, CHCl$_3$)

IR$\nu_{max}^{CHCl_3}$ (cm$^{-1}$): 1730, 1600

NMR (CDCl$_3$) δ: 0.72 (3H, s, CH$_3$); 1.01 (3H, s, CH$_3$); 1.26 (3H, d, J=7 Hz, CH$_3$); 1.29 (3H, d, J=7 Hz, CH$_3$); 2.05 (3H, s, CH$_3$); 2.79 (1H, t, J=2.5 Hz, CH); 3.34 (3H, s, OCH$_3$); 3.57 (3H, s, OCH$_3$); 5.13 and 5.18 (each 1H, each d, J=6 Hz, OCH$_2$O).

MS m/z: 498 (M+)

Elemental analysis: Calc. C 74.66; H 9.30; Found C 74.39; H 9.51.

1.2 g of the compound (5) prepared as mentioned above was treated in accordance with the procedure same as that of the Example 3 so as to obtain 1.09 g of the compound (6) (yield 90%).

EXAMPLE 5

Synthesis of (20E)-6β-methoxy-23-methoxymethoxy-3α,5-cyclo-5α-ergost-20(22),23-dieno-28,22-lactone [compound (7)]

7 g of the compound (4) prepared in the Example 2 was dissolved into 100 ml of benzene, and 2.4 ml of DBU was added thereto. The obtained mixture was heated while refluxing for 15 min. The reaction liquid was washed with water, and after drying with Na2SO4, the solvent was distilled. 4.8 g of the desired compound (7) was obtained as a mixture with 1.7 g of the compound (5) (yield 69%). The compound (7) was isolated from the mixture by chromatography with silica gel column.

mp 147°–147.5° C.

$[\alpha]_D$+12.3° (c=0.57, CHCl3)

IR$\nu_{max}^{CHCl3}$ (cm$^{-1}$): 1730, 1610

NMR (CDCl3) δ: 0.75 (3H, s, CH3); 1.03 (3H, s, CH3); 1.27 (6H, d, J=7 Hz, 2×CH3); 1.95 (3H, s, CH3); 2.80 (1H, t, J=2.5 Hz, CH); 3.34 (3H, s, OCH3); 3.56 (3H, s, OCH3); 5.13 and 5.23 (each 1H, each d, J=6 Hz, OCH2O).

MS m/z: 498 (M+)

Elemental analysis: Calc. C 74.66; H 9.30; Found C 74.60; H 9.50.

EXAMPLE 6

Synthesis of (22R)-6β-methoxy-23-methoxymethoxy-3α,5-cyclo-5α-ergost-23-eno-28,22-lactone [compound (9)]

100 mg (0.2 mmol) of the compound (5) prepared in the Example 4 was dissolved into AcOEt (4 ml), and 5% Rh-Al2O3 (50 mg) was added thereto. The obtained suspension was shaken for 5 hours under H2 (4 atm.) atmosphere. The reaction liquid was filtered and then the solvent was distilled from the filtrate. The residue was recrystallized from MeOH, and 95 mg (yield 95%) of the compound (9) of colorless crystal having mp 157°–158° C. was obtained.

$[\alpha]_D$+52.9° (c=0.49, CHCl3)

IR$\nu_{max}^{CHCl3}$ (cm$^{-1}$): 1740, 1650

$^1$HNMR (100 MHz) δ: 0.75 (3H, s, 18-H3); 0.77 (3H, d, J=7 Hz, 21-H3); 1.02 (3H, s, 19-H3); 1.22 (6H, d, J=7 Hz, 26-H3 and 27-H3); 2.78 (1H, t, J=2.5 Hz, 6-H); 2.70–3.00 (1H, m, 25-H); 3.33 (3H, s, 6-OMe); 3.52 (3H, s, OCH2OCH3); 4.86 (1H, d, J=2 Hz, 22-H); 5.05 and 5.21 (each 1H, each d, J=6 Hz, OCH2OCH3).

MS m/z: 500 (M+)

Elemental analysis: Calc. C 74.36; H 9.66; Found C 74.27; H 9.96.

The reduction using 100 mg of the compound (4) prepared in the Example 2 was carried out in the same manner with those mentioned above so as to obtain 93 mg of the compound (9) (yield 93%).

EXAMPLE 7

Synthesis of (22S,23S,24R)-6β-methoxy-23-methoxymethoxy-3α,5-cyclo-5α-ergostan-28,22-lactone [compound (8)]

Using 1.2 g of the compound (7) prepared in the Example 5, the reaction was carried out in the same manner with that of the Example 3 to obtain 1.1 g of the desired compound (8) (yield 92%).

$[\alpha]_D$+24.7° (c=2.02, CHCl3)

IR$\nu_{max}^{CHCl3}$ (cm$^{-1}$): 1770

NMR (CDCl3) δ: 0.76 (3H, s, CH3); 1.02 (3H, s, CH3); 1.05 (3H, d, J=7 Hz, CH3); 1.07 (3H, d, J=7 Hz, CH3); 1.27 (3H, d, J=7 Hz, CH3); 2.18 (1H, dd, J=8 Hz, 4 Hz, CH); 2.77 (1H, t, J=2.5 Hz, CH); 3.32 (3H, s, OCH3); 3.41 (3H, s, OCH3); 3.93 (1H, dd, J=8 Hz, 2 Hz, CH); 4.36 (1H, dd, J=4 Hz, 2.5 Hz, CH); 4.71 and 4.73 (each 1H, each d, J=7 Hz, OCH2O).

MS (C31H50O5): Calc. 502.3657; Found 502.3656.

EXAMPLE 8

Synthesis of (22S)-6β-methoxy-23-methoxymethoxy-3α,5-cyclo-5α-ergost-23-eno-28,22-lactone [compound (10)]

Using 100 mg (0.2 mmol) of the compound (7) prepared in the Example 5, the reduction was carried out in accordance with the procedure of the Example 6, and 97 mg of the compound (10) (yield 97%) was obtained.

$[\alpha]_D$+24.0° (c=0.43, CHCl3)

IR$\nu_{max}^{CHCl3}$ (cm$^{-1}$): 1740, 1640

$^1$HNMR (100 MHz) δ: 0.75 (3H, s, 18-H3); 0.91 (3H, d, J=7 Hz, 21-H3); 1.02 (3H, s, 19-H3); 1.24 (6H, d, J=7 Hz, 26-H3 and 27-H3); 2.78 (1H, t, J=2.5 Hz, 6-H); 2.78–3.12 (1H, m, 25-H); 3.33 (3H, s, 6-OMe); 3.55 (3H, s, OCH2OCH3); 4.68 (1H, d, J=3 Hz, 22-H); 5.12 and 5.25 (each 1H, each d, J=6 Hz, OCH2OCH3).

MS (C31H48O5): Calc. 500.3502; Found 500.3504.

Now, examples of synthesis of γ-lactone derivative having the general formula (I) in which St represents steroid nucleus of the B type are described below.

Reference 2

Synthesis of brassinolide from compound (6)

(i) Preparation of (22R,23R,24R)-22,28-dihydroxy-6β-methoxy-23-methoxymethoxy-3α,5-cyclo-5α-ergostane [compound (11)]

1.7 g of compound (6) obtained in the Example 3 was dissolved in 130 ml of THF, and after 390 mg of LiAlH4 was added thereto, the obtained mixture was stirred at room temperature for 20 min. 10 ml of 25% NaOH aq. solution was added to the reaction liquid and the mixture was extracted with AcOEt. The extract was washed with water and dried with Na2SO4, and then the solvent was distilled, thereby obtaining 1.7 g (yield 98%) of compound (11).

IR$\nu_{max}^{CHCl3}$ (cm$^{-1}$): 3400

NMR (CDCl3) δ: 0.71 (3H, s, CH3); 0.87 (3H, d, J=7 Hz, CH3); 1.00 (3H, d, J=7 Hz, CH3); 1.02 (3H, s, CH3); 1.06 (3H, d, J=7 Hz, CH3); 2.77 (1H, t, J=2.5 Hz, CH); 3.33 (3H, s, OCH3); 3.45 (3H, s, OCH3); 4.68 and 4.81 (each 1H, each d, J=6 Hz, OCH2O).

MS m/z: 505 (M+−1)

(ii) Preparation of (22R,23R,24S)-22-hydroxy-6β-methoxy-23-methoxymethoxy-3α,5-cyclo-5α-ergostane [compound (12)]

0.17 ml of MeSO$_2$Cl was added to a solution containing 1 g of compound (11) and 0.3 ml of Et$_3$N in 30 ml of CH$_2$Cl$_2$ and the obtained mixture was stirred for 10 min. at 0° C. while cooling with ice. 10 ml of saturated NaHCO$_3$ aq. solution was added to the reaction liquid and the obtained mixture was extracted with AcOEt. The extract was washed with water and dried with Na$_2$SO$_4$, and the solvent was distilled.

The obtained residue was dissolved in 50 ml of Et$_2$O, and after 500 mg of LiAlH$_4$ was added thereto, the mixture was stirred at room temperature for 30 min. Thereafter, 5 ml of 25% NaOH aq. solution was added to the reaction liquid, and the mixture was extracted with AcOEt. The extract was washed with water and dried with Na$_2$SO$_4$, and then the solvent was distilled therefrom. As a result of treatment of the residue with silica gel column-chromatography, 810 mg (yield 84%) of compound (12) was obtained.

mp 117.5°–119° C.
$[\alpha]_D$ +12.1° (c=1.19, CHCl$_3$)
IR$\nu_{max}^{CHCl3}$ (cm$^{-1}$): 3400
NMR (CDCl$_3$) δ: 0.73 (3H, s, CH$_3$); 0.87 (3H, d, J=7 Hz, CH$_3$); 0.89 (3H, d, J=7 Hz, CH$_3$); 0.93 (3H, d, J=7 Hz, CH$_3$); 0.94 (3H, d, J=7 Hz, CH$_3$); 1.03 (3H, s, CH$_3$); 2.77 (1H, t, J=2.5 Hz, CH); 3.33 (3H, s, OCH$_3$); 3.43 (3H, s, OCH$_3$); 3.56 (1H, d, J=9 Hz, CH); 3.59 (1H, d, J=9 Hz, CH); 4.70 and 4.72 (each 1H, each d, J=6 Hz, OCH$_2$O).
MS m/z: 490 (M$^+$)
Elemental analysis: Calc. C 75.87; H 11.09; Found C 75.65; H 11.39.

(iii) Preparation of (22R,23R,24S)-3β,22,23-trihydroxyergost-5-ene [compound (13)]

500 mg of compound (12) was dissolved in Ac$_2$O (2 ml)—pyridine (10 ml) mixture and after 4-(N,N-dimethylamino)pyridine was added in catalytic amount thereto, the mixture was stirred at room temperature for 12 hours. The reaction liquid was poured into water and the mixture was extracted with Et$_2$O. The extract was washed with water and dried with Na$_2$SO$_4$, and the solvent was distilled therefrom.

The obtained monoacetate was dissolved in dioxane (15 ml)—water (2.3 ml) mixture, 90 mg of p-TsOH was added thereto, and the mixture was stirred at 80° C. for 1 hour. The reaction liquid was extracted with AcOEt and the obtained extract was washed with water and dried with Na$_2$SO$_4$, and the solvent was distilled therefrom, thereby obtaining 410 mg of 3β,22-diol.

200 mg of the obtained 3β,22-diol was dissolved in 10 ml of 5% KOH-MeOH solution and the mixture was heated for 1 hour while refluxing. The reaction liquid was extracted with AcOEt, and the extract was washed with water and dried with Na$_2$SO$_4$, and the solvent was distilled therefrom, whereby 170 mg (yield 97%) of compound (13) was obtained as colorless prism crystal having mp 206°–208° C.

The various spectral data of this product were accorded with those described in the literature [J. Ame. Chem. Soc. 102, 6580 (1980)].

(iv) Preparation of brassinolide

The transformation from compound (13) to brassinolide was carried out in accordance with the method described in J. Ame. Chem. Soc. 102, 6580 (1980).

Reference 3
Synthesis of epibrassinolide from compound (8)

(i) Preparation of (22S,23S,24S)-22,28-dihydroxy-6β-methoxy-23-methoxymethoxy-3α,5-cyclo-5α-ergostane [compound (14)]

Using 1.1 g of compound (8) obtained in the Example 7, the reaction same as that of the step (i) of the Reference 2 was carried out according with the procedure described therein. As a result, 1.1 g (yield 99%) of compound (14) was obtained.

IR$\nu_{max}^{CHCl3}$ (cm$^{-1}$): 3400
NMR (CDCl$_3$) δ: 0.75 (3H, s, CH$_3$); 1.02 (3H, s, CH$_3$); 1.03 (9H, d, J=7 Hz, 3×CH$_3$); 2.77 (1H, t, J=2.5 Hz, CH); 3.23 (3H, s, OCH$_3$); 3.45 (3H, s, OCH$_3$); 4.70 and 4.77 (each 1H, each d, J=6 Hz, OCH$_3$O).
MS m/z: 505 (M$^+$−1)

(ii) Preparation of (22S,23S,24R)-22-hydroxy-6β-methoxy-23-methoxymethoxy-3α,5-cyclo-5α-ergostane [compound (15)]

Using 1.1 g of compound (14), the reaction same as that of step (ii) of Reference 2 mentioned above was carried out according to the procedure described therein. As a result 863 mg (yield 80%) of compound (15) was obtained.

$[\alpha]_D$ +29.5° (c=1.06, CHCl$_3$)
IR$\nu_{max}^{CHCl3}$ (cm$^{-1}$): 3400
NMR (CDCl$_3$) δ: 0.75 (3H, s, CH$_3$); 0.89 (3H, d, J=7 Hz, CH$_3$); 0.91 (3H, d, J=7 Hz, CH$_3$); 0.96 (3H, d, J=7 Hz, CH$_3$); 1.02 (3H, s, CH$_3$); 1.03 (3H, d, J=7 Hz, CH$_3$); 2.77 (1H, t, J=2.5 Hz, CH); 3.32 (3H, s, OCH$_3$); 3.43 (3H, s, OCH$_3$); 3.64 (1H, dd, J=6 Hz, 2.5 Hz, CH); 4.67 and 4.73 (each 1H, each d, J=6 Hz, OCH$_2$O).
MS m/z: 489 (M$^1$−1)

(iii) Preparation of (22S,23S,24R)-3β,22,23-trihydroxyergost-5-ene [compound (16)]

Using 1.1 g of compound (15), the reaction same as that of the step (iii) of Reference 2 mentioned above was carried out. 752 mg (yield 80%) of compound (16) was obtained.

mp 165.5°–167° C.
$[\alpha]_D$ −44.6° (c=0.69, CHCl$_3$)
IR$\nu_{max}^{CHCl3}$ (cm$^{-1}$): 3400
NMR (CDCl$_3$) δ: 0.71 (3H, s, CH$_3$); 0.88 (3H, d, J=7 Hz, CH$_3$); 0.91 (3H, d, J=7 Hz, CH$_3$); 0.97 (3H, d, J=7 Hz, CH$_3$); 1.01 (3H, s, CH$_3$); 1.02 (3H, d, J=7 Hz, CH$_3$); 3.60 (1H, dd, J=3 Hz, 3 Hz, CH); 3.73 (1H, dd, J=4 Hz, 3 Hz, CH).
MS m/z: 432 (M$^+$)
Elemental analysis: Calc. C 77.72; H 11.18; Found C 77.36; H 11.28.

(iv) Preparation of (22S,23S,24R)-22,23-isopropylidenedioxy-5α-ergost-2-en-6-one [compound (17)]

20 mg of p-TsOH was added to a solution containing 160 mg of compound (16) in 2 ml of acetone and the mixture was stirred at room temperature for two hours.

20 ml of AcOEt was added thereto. The mixture was washed with saturated NaHCO3 aq. solution and dired with Na2SO4, and the solvent was distilled therefrom.

The residue was dissolved in 2 ml of pyridine, 0.06 ml of MeSO2Cl was added thereto, and the obtained mixture was stirred at room temperature for 1 hour. Thereafter, the reaction liquid was poured into water and was extracted with Et2O. The extract was washed with water and dried with Na2SO4, and then the solvent was distilled.

The obtained residue was dissolved in 3 ml of THF, 1 ml of BH3-THF solution was added thereto, and the mixture was stirred at room temperature for 2 hours. Thereafter, 0.5 ml of 10% NaOH aq. solution and 0.7 ml of 30% H2O2 were added thereto and the mixture was stirred at room temperature for 20 min. The reaction liquid was extracted with AcOEt, the extract was washed with water and dried with Na2SO4, and the solvent was distilled.

The residue was dissolved in 8 ml of CH2Cl2, 150 mg of pyridinum chlorochromate (PCC) was added thereto, and the mixture was stirred at room temperature for 2 hours. 20 ml of Et2O was added to the reaction liquid, the mixture was washed with water and dried with Na2SO4, and the solvent was distilled.

The obtained residue was dissolved in 3 ml of DMF, 54 mg of LiBr was added thereto, and the mixture was heated at 130° C. for 1 hour. The reaction liquid was poured into water and extracted with Et2O, the extract was washed with water and dried with Na2SO4, and then the solvent was distilled. As a result of treatment of the residue with silica gel column-chromatography, 95 mg (yield 63%) of compound (17) was obtained.

mp 181°–182° C.
$[\alpha]_D + 0.9°$ (c=0.21, CHCl3)
$IR\nu_{max}^{CHCl_3}$ (cm$^{-1}$): 1710
NMR (CDCl3) δ: 0.70 (3H, s, CH3); 0.71 (3H, s, CH3); 1.34 (3H, s, CH3); 1.37 (3H, s, CH3).
MS (C30H46O4): Calc. 470.3398; Found 470.3388.

(v) Preparation of (22S,23S,24R)-2α,3α,22,23-tetrahydroxy-5α-ergostan-6-one [compound (18)]

75 mg of compound (17) was dissolved in 5 ml of ′BuOH-THF-H2O (10:8:1), 56 mg of N-methyl morpholine and 7.5 mg of OsO4 were added thereto, and the obtained mixture was stirred at room temperature for 3 hours. The reaction liquid was extracted with AcOEt, and the extract was washed with saturated NaHCO3 aq. solution and saturated NaCl aq. solution and dried with Na2SO4, and then the solvent was distilled.

The residue was dissolved in AcOH (2 ml)—H2O (0.7 ml) and the obtained solution was heated for 3 hours while refluxing. The reaction solution was extracted with AcOEt, the extract was washed with saturated NaHCO3 aq. solution and dried with Na2SO4, and the solvent was distilled. As a result of residue with silica gel column-chromatography, 62 mg (yield 84%) of compound (18) was obtained.

The spectral data of compound (18) were accorded with those described in the literature [J. Org. Chem. 44, 5003 (1979)].

(vi) Preparation of epibrassinolide

The transformation of the compound (18) to epibrassinolide was carried out in accordance with the method described in J. Ame. Chem. Soc. 102, 6580 (1980).

Reference 4

Synthesis of (2R,3S)-6,6-ethylenedioxy-2,3-isopropylidenedioxy-5α-pregn-5-en-20-one [compound (1′)]

(2R,3S)-6,6-ethylenedioxy-2,3-isopropylidenedioxy-5α-pregn-5-en-20-one [compound (1′)] which is one of the starting materials was synthesized through the following reaction process.

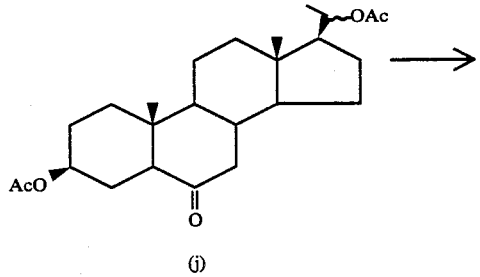

(j)

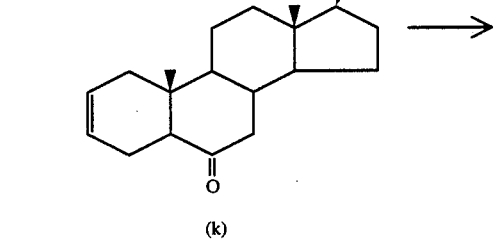

(k)

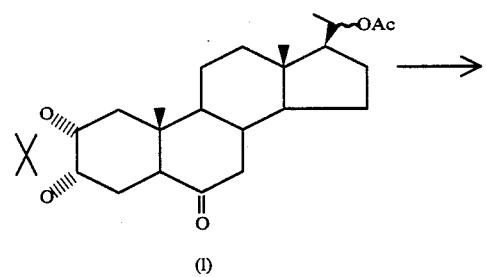

(l)

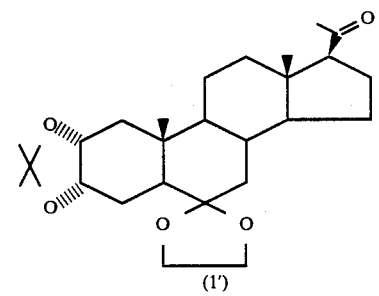

(1′)

(i) Synthesis of 20 R/S-acetoxy-5α-pregn-2-en-6-one [compound (k)]

26 ml of 5% KOH aq. solution was added to 400 ml of solution containing in MeOH 12 g of 3β,20ξ-diacetoxy-5α-pregn-6-one (j) (described in J. Org. Chem. 51, 2932 (1986)), and the mixture was stirred for one hour at room temperature. 10% HCl was added to the reaction liquid to neutralize while cooling with ice, and the neutralized reaction liquid was extracted with AcOEt. The extract was then washed with water, dried with Na₂SO₄, and the solvent was distilled thereafter. The residue was dissolved into 90 ml of pyridine, 2.9 ml of MsCl was added thereto while cooling with ice, and the mixture was stirred for one hour at room temperature. The saturated NaHCO₃ aq. solution was added to the reaction liquid, and the obtained mixture was extracted benzene. The extract was then washed with water, dried with Na₂SO₄, and the solvent was distilled thereafter. The residue was dissolved into 190 ml of DMF, LiBr 6 g was added thereto, and the mixture was heated while refluxing for one hour. The saturated NaHCO₃ aq. solution was added to the reaction liquid, and the mixture was extracted with benzene thereafter. The extract was then washed with water, dried with Na₂SO₄, and the solvent was distilled thereafter. As a result of a treatment of the residue with silica gel co-lumn-chromatography, 8.45 g (yield 80%) of the desired compound (k) was obtained.

IR $\nu_{max}^{CHCl_3}$ (cm⁻¹): 1710, 1720

(ii) Synthesis of (2R,3S,20R/S)-20-acetoxy-2,3-isopropylidenedioxy-5α-pregn-6-one [compound (1)]

8 g of the compound (k) obtained by the process mentioned above was dissolved into 200 ml of a mixture of tBuOH-THF-H₂O (10:8:1), 9 g of N-methylmorpholine-N-oxide and 985 mg of OsO₄ were added thereto, and the mixture was stirred for 3 hours at room temperature.

The reaction liquid was then extracted with AcOEt, the extract was washed with saturated NaHSO₃ aq. solution and saturated NaCl water, dried with Na₂SO₄, and the solvent was distilled thereafter.

The residue was then dissolved into 200 ml of acetone, 20 g of p-TsOH was added thereto, and the mixture was stirred for 2 hours at room temperature. The saturated NaHCO₃ aq. solution was added to the reaction liquid, and the mixture was extracted with benzene. After washing the extract with water, dired with Na₂SO₄, and the solvent was distilled.

As a result of a treatment of the residue with silica gel column-chromatography, 8.05 g (yield 85%) of the desired compound (1) was obtained.

IR $\nu_{max}^{CHCl_3}$ (cm⁻¹): 1710, 1720

(iii) Synthesis of the compound (1')

200 mg of p-TsOH was added to 40 ml of a solution containing 7 g of the compound (1) obtained as above in 2,2-dimethyl-1,3-dioxolane and the mixture was heated for 2 hours while refluxing. The saturated NaHCO₃ solution was then added to the reaction liquid, and the mixture was extracted with benzene. The extract was then washed with water, dried with Na₂SO₄, and the solvent was distilled.

The residue was dissolved in 100 ml of 5% KOH-MeOH solution, and the obtained solution was heated for one hour while refluxing. The reaction liquid was then neutralized with 10% HCl, and extracted with EtOAc. The extract was washed with water, dried with Na₂SO₄, and the solvent was distilled thereafter. The residue was dissolved into 200 ml of CH₂Cl₂, 6.2 g of PCC was added thereto, and the mixture was stirred for 2 hours at room temperature.

The reaction liquid was washed with water dried with Na₂SO₄, and the solvent was distilled thereafter. As a result of a treatment of the residue with silica gel column-chromatography, 5.6 g (yield 88%) of the desired compound (1') was obtained.

IR $\nu_{max}^{CHCl_3}$ (cm⁻¹): 1700

NMR (CDCl₃) δ: 0.62 (s, 3H, Me); 0.84 (s, 3H, Me); 1.32 (s, 3H, Me); 1.48 (s, 3H, Me); 2.12 (s, 3H, Me); 3.72–4.00 (m, 4H, —OCH₂CH₂O—); 4.10 (s, 1H, 2-H); 4.27 (s, 1H, 3-H).

MS m/z: 432 (M+)

Example 9

Synthesis of (2R,3S,20R,22R)-6,6-ethylendioxy-20-hydroxy-2,3-isopropylidenedioxy-23-methoxymethoxy-5α-ergost-23-eno-28,22-lactone [compound (3')]

24 ml of anhydrous THF solution of 2.4 g of the compound (1'), obtained by the process described at −78° C. to 36 ml of anhydrous THF solution of 2,4-dilithiooxy-3-isopropylfuran prepared from 3.8 g of 3-isopropyltetronic acid obtained in the above-mentioned Reference 1 and lithium isopropylamide. The reaction liquid was stirred for one hour while maintaining the temperature of 78° C.

20 ml of saturated NH₄Cl aq. solution was added to the reaction liquid, the mixture was extracted with AcOEt, the extract liquid was then washed with saturated NaCl solution, dried with Na₂SO₄, and the solvent was distilled.

The residue was dissolved into 42 ml of DMF, 1.5 g of K₂CO₃ was added thereto, and the mixture was stirred for 2 hours at the temperature of 100° C. 0.46 ml of chrolomethylmethyl ether was then added thereto, and the mixture was stirred for one hour at the temperature of 50° C. AcOEt was added to the reaction liquid, the mixture was washed with saturated NaCl solution, dried with Na₂SO₄, and the solvent was distilled thereafter.

As a result of a treatment of the residue with silica gel column-chromatography, 30 g (yield 88%) of compound (3') was obtained, which has the following structure:

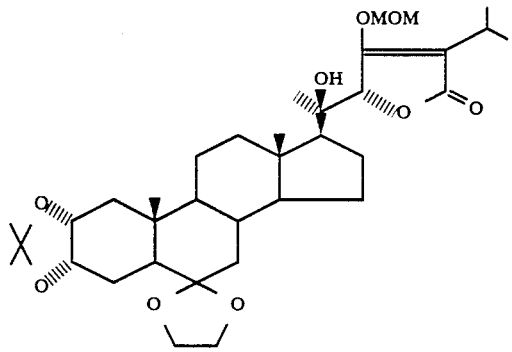

$[\alpha]_D^{25}$ +33.07° (c=1.01, CHCl₃)
IR $\nu_{max}^{CHCl_3}$ (cm⁻¹): 3400, 1740, 1660
NMR (CDCl₃) δ: 0.83 (s, 3H, Me); 0.87 (s, 3H, Me); 1.19 (s, 3H, Me); 1.23 (d, J=7 Hz, 2×Me); 1.33 (s, 3H, Me); 1.49 (s, 3H, Me); 2.85–2.95 (m, 1H, 25-H); 3.53 (s, 3H, OCH₃); 3.70–4.00 (m, 4H, —OCH₂CH₂O—); 4.10 (1H, br 2-H); 4.27 (1H, br s, 3-H); 4.65 (s, 1H, 22-H); 5.06 and 5.44 (each 1H, each d, J=6 Hz, OCH₂O).
MS m/z: 618 (M+)
High MS (C₃₅H₅₄O₉): Calc. 618.3765; Found 618.3759.

Example 10

Synthesis of (2R,3S,20Z)-6,6-ethylenedioxy-2,3-isopropylidenedioxy-23-methoxymethyoxy-5'-ergost-20(22),23-dieno-28,22-lactone [compound (5')]

1.35 ml of (CF$_3$CO)$_2$O was added, while cooling with ice, to 20 ml of CH$_2$Cl$_2$ solution containing the compound (3') obtained by the process described in the Example 9, 0.93 ml of Et$_3$N, and 141 mg of PPY, and the obtained mixture was stirred for one hour at room temperature. The saturated NaHCO$_3$ aq. solution was then added to the reaction liquid and the mixture was extracted with benzene. The extract was washed with water and dried with Na$_2$SO$_4$, and the solvent was distilled thereafter. The residue was dissolved into 60 ml of benzene, 0.72 ml of DBU was added thereto and the mixture was heated for 30 min. while refluxing. The reaction liquid was extracted with benzene, and the extract was washed with water, dried with Na$_2$SO$_4$, and the solvent was distilled thereafter.

As a result of a treatment of the residue with silica gel column- chromatography, 787 ml (yield 81%) of the compound (5') having the following structural formula was obtained.

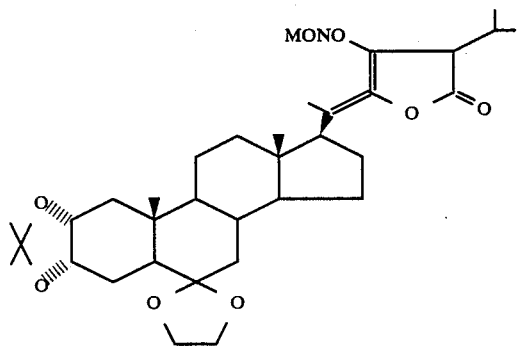

$[\alpha]_D^{25}$ −27.80° (c=1.09, CHCl$_3$)
IR $\nu_{max}^{CHCl_3}$ (cm$^{-1}$): 1730, 1600
NMR (CDCl$_3$) δ: 0.67 (3H, s, Me); 0.83 (3H, s, Me); 1.25 (3H, d, J=7 Hz, Me); 1.28 (3H, d, J=7 Hz, Me); 1.32 (3H, s, Me); 1.48 (3H, s, Me); 2.04 (3H, s, Me); 2.90–3.05 (1H, m, 25-H); 3.56 (3H, s, Me); 3.70–4.00 (4H, m, —OCH$_2$CH$_2$O—); 4.10 (1H, br 2-H); 4.27 (1H, br s, 3-H); 5.17 and 5.20 (each 1H, each d, J=6 Hz, —OCH$_2$O—)
MS m/z: 600 (M$^+$)
High MS (C$_{35}$H$_{52}$O$_8$): Calc. 600.3660; Found 600.3645.

Example 11

Synthesis of (2R,3S,22R,23R,24S)-6,6-ethylenedioxy-2,3-isopropylidenedioxy-23-methoxymethoxy-5α-ergostano-28,22-lactone [compound (60')]

200 mg of 5% Rh-Al$_2$O$_3$ was added to 20 ml of AcOEt solution containing 500 mg of the compound (5') obtained by the process described in the Example 10, and the mixture was shaked for 15 hours in the hyrodgen atmosphere (7 atm.). After the reactikon liquid was filtrated, the solvent was distilled from the extract, whereby 460 mg (yield 92%) of a compound having the following structural formula was obtained.

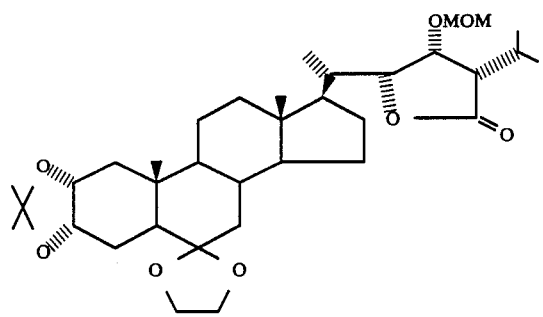

$[\alpha]_D^{25}$ +43.33° (c=0.57, CHCl$_3$)

IR $\nu_{max}^{CHCl_3}$ (cm$^{-1}$): 1760

NMR (CDCl$_3$) δ: 0.71 (s, 3H, Me); 0.83 (s, 3H, Me); 1.07 (d, 3H, J=7 Hz, Me); 1.14 (d, 3H, J=7 Hz, Me); 1.24 (d, 3H, J=7 Hz, Me); 1.33 (s, 3H, Me); 1.48 (s, 3H, Me); 2.10–2.20 (1H, m, H); 2.10–2.20 (1H, m, H); 2.28 (1H, dd, J=8.5 Hz, H); 3.41 (3H, s, Me); 3.70–4.00 (4H, m, —OCH$_2$CH$_2$O); 4.10 (1H, br 2-H); 4.22 (1H, dd, J=3.5, 1.5 Hz, 23-H); 4.27 (1H, br s, 3-H); 4.32 (1H, dd, J=5.35 Hz, 22-H); 4.67 and 4.73 (each 1H, each d, J=6 Hz, —OCH$_2$O).

MS m/z: 604 (M$^+$)

High MS (C$_{35}$H$_{56}$O$_8$): Calc. 604.3973; Found 604.3972.

Next, examples of synthesis of γ-lactone derivative having the above-mentioned general formula (I) in which R$^7$ is methyl group, which can be used as a raw material in the synthesis of bisnorbrassinolide, are described below.

The consecutive reaction in this case is as follows:

reaction process

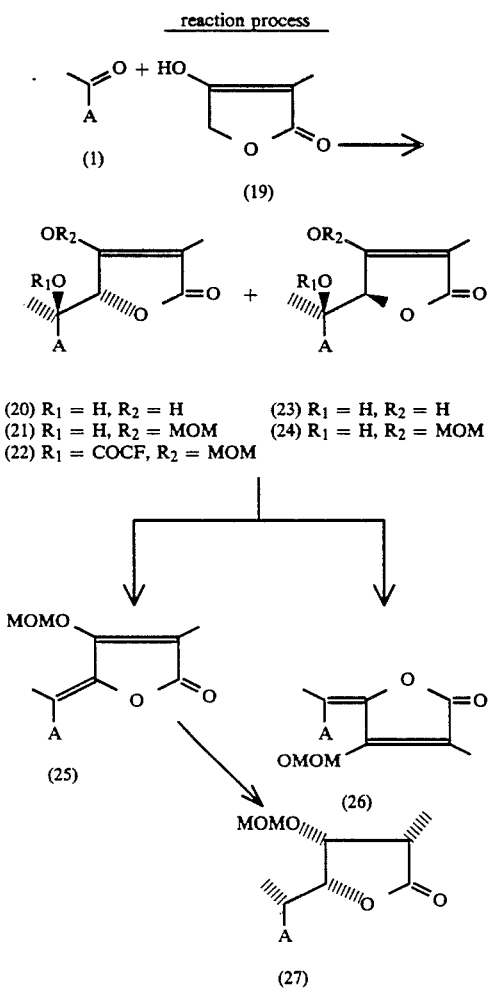

(20) R₁ = H, R₂ = H
(21) R₁ = H, R₂ = MOM
(22) R₁ = COCF, R₂ = MOM
(23) R₁ = H, R₂ = H
(24) R₁ = H, R₂ = MOM

Example 12

Synthesis of (20R,22R)-20-hydroxy-6β-methoxy-23-methoxymethoxy-3α,5-cyclo-5α-24-norcholest-23-eno-26,22-lactone [compound (21)] and (20R,22S)-isomer [compound (24)]

(i) Preparation of 3-methyltetronic acid [compound (19)]

100 g of α-methylacetoacetic acid ethyl ester was dissolved in 350 ml of CHCl₃, a solution containing 117 g (0.73 mol) of Br₂ 117 g in CHCl₃ (100 ml) was added thereto while cooling with ice, and the obtained mixture was stirred for one hour at room temperature. The solvent was distilled and the residue was heated for 2 hours at 130° C. After cooling the residue, the deposited crystal was washed with hexane and a recrystallization was carried our from MeOH.

As a result, 54 g (yield 68) of compound (19) was obtained as a colorless needle-like crystal having the mp of 189°–190° C. The mp and various spectral characteristics were corresponded with data described in J. Chem. Soc. 1955, 588.

(ii) Synthesis of the compounds (21) and (24)

10 g (87.7 mmol) of the compound (19) prepared as above was dissolved in THF (80 ml), and a solution containing LiN(isopropyl)₂ (175.4 mmol) in THF (80 ml was added at the temperature of −78° C. thereto, and in addition, THF solution (80 ml) of 6 g (18.2 mmol) of 6β-methoxy-3α,5-cyclo-pregnen-20-one(1) was also added thereto. The obtained mixture was stirred for one hour at same temperature. The saturated NH₄Cl aq. solution was then added to the reaction liquid. The mixture was extracted with AcOEt, the extract was washed with saturated NaHCO₃ aq. solution and saturated NaCl solution, dried with Na₂SO₄, and solvent was distilled thereafter.

The mixture of compounds (20) and (23) obtained as above was dissolved in DMF (100 ml), 3 g (21.7 mmol) of K₂CO₃ was added thereto, the mixture was heated at the temperature of 70° C. for 2 hours. Thereafter, 1.61 ml (19.94 mmol) of MeOCH₂Cl was added to the mixture. Thus obtained mixture was stirred for 10 minutes at the temperature of 50° C. 200 ml of AcOEt was added to the reaction liquid. The mixture was washed with saturated KHSO₄ aq. solution and saturated NaCl solution, dried with Na₂SO₄, and the solvent was distilled thereafter.

As a result of a treatment of the residue with silica gel column-chromatography, 6.53 g (yield 74%) of the compound (21) was obtained from benzene elution part as a colorless prism crystal having the mp of 131.5°–133° C. (MeOH).

$[α]_D + 20.08°$ (c=0.87, CHCl₃)

IR $ν_{max}^{CHCl_3}$ (cm⁻¹): 1750, 1660

NMR (CDCl₃) δ: 0.93 (3H, s, 18-H₃); 1.02 (3H, s, 19-H₃); 1.20 (3H, s, 21-H₃); 1.93 (3H, d, J=1 Hz, 27H₃); 2.76 (1H, t, J=2.5 Hz, 6-H); 3.32 (3H, s, 6-OMe); 3.55 (3H, s, OCH₂OMe); 4.57 (1H, d, J=1 Hz, 22-H); 5.29 and 5.37 (each 1H, each d, J=6 Hz, —OCH₂OMe).

MS m/z: 488 (M⁺)

Elemental analysis (C₂₉H₄₄O₆): Calc. C 71.28; H 9.08; Found C 71.28; H 9.27.

Additionally, 1.08 g (yield 12%) of the compound (24) was obtained from benzene elution part as a colorless amorphous solid.

$[α]_D^{25} + 18.18°$ (c=1.11, CHCl₃)

IR $ν_{max}^{CHCl_3}$ (cm⁻¹): 1750, 1660

¹NMR (100M Hz) δ: 0.93 (3H, s, 18-H₃); 1.02 (3H, s, 19-H₃); 1.19 (3H, s, 21-H₃); 1.94 (3H, d, J=1 Hz, 27H₃); 2.76 (1H, t, J=2.5 Hz, 6-H); 3.33 (3H, s, 6-OMe); 3.56 (3H, s, OCH₂OMe); 4.59 (1H, d, J=1 Hz, 22-H); 5.23 and 5.34 (each 1H, each d, J=6 Hz, —OCH₂OMe).

MS (C₂₉H₄₄O₆): Calc. 488.3135; Found 488.3104.

Example 13

Synthesis of (20Z)-6β-methoxy-23-methoxymethoxy-3α,5-cyclo-5α-24-norcholest-20(22),23-dieno-26,22-lactone [compound (25)] and (20E-isomer [compound (26)]

6.5 g (13.1 mmol) of the compound (21) which was obtained by the process described in the above Example 12, 5.55 ml (40 mmol) of Et₃N and 590 mg (4 mmol) of 4-pyrrolidinopyridine were dissolved in 100 ml of CH₂Cl₂, and 5.65 ml (40 mmol) of (CF₃CO)₂O was added dropwise thereto. After the mixture was stirred for one hour at room temperature, it was poured into ice water, and the mixture was extracted with CH₂Cl₂.

The extract was washed with saturated NaCl solution, and after it was dried with Na₂SO₄, the solvent was distilled, whereby 7.24 g (yield 93%) of the compound (22) was obtained.

IR $ν_{max}^{CHCl_3}$ (cm⁻¹): 1780, 1750, 1660

¹NMR (100 MHz) δ: 0.87 (3H, s, 18-H₃); 1.01 (3H, s, 19-H₃); 1.73 (3H, s, 21-H₃); 1.96 (3H, d, J=1 Hz, 27H₃); 2.76 (1H, t, J=2.5 Hz, 6-H); 3.31 (3H, s, 6-OMe); 3.52 (3H, s, OCH₂OMe); 5.21 (3H, br s, OCH₂OMe and 22-H).

MS (C₃₁H₄₃O₇F₃): Calc. 584.2948; Found 584.2959.

7.25 g (12.4 mmol) of the compound (22) obtained by preparation described above and 2.08 ml (13.6 mmol) of DBU were dissolved in 200 ml of benzene and the obtained solution was heated while refluxing. After cooling reaction liquid, it was washed with saturated KHSO₄ aq. solution and saturated NaCl solution, dried with Na₂SO₄ and the solvent was distilled thereafter.

As a result of a treatment of the residue with silica gel column-chromatography, 4.67 g (yield 80%) of the compound (25) was obtained from benzene elution part as a colorless prism crystal having the mp of 174°–175° C. (MeOH-CH₂Cl₂).

$[\alpha]_D$ −134.1° (c=1.32, CHCl₃)
IR $\nu_{max}^{CHCl_3}$ (cm⁻¹): 1730, 1620
¹HNMR (100 MHz) δ: 0.72 (3H, s, 18-H₃); 1.01 (3H, s, 19-H₃); 2.00 (3H, s, 27-H₃); 2.06 (3H, s, 21-H₃); 2.77 (1H, t, J=2.5 Hz, 6-H); 3.33 (3H, s, 6-OMe); 3.54 (3H, s, OCH₂OMe); 5.27 and 5.35 (each 1H, each d, J=6 Hz, OCH₂OMe).

Elemental analysis: Calc. C 74.01; H 9.00; Found C 73.75; H, 9.23.

In addition 0.41 g (yield 7%) of the compound (26) was also obtained from benzene elution part as a colorless amorphous solid.

$[\alpha]_D$ +10.0° (c=1.09, CHCl₃)
IR $\nu_{max}^{CHCl_3}$ (cm⁻¹): 1730, 1620
¹HNMR (100 MHz) δ: 0.75 (3H, s, 18-H₃); 1.03 (3H, s, 19-H₃); 1.96 (3H, s, 21-H₃); 2.00 (3H, s, 25-H₃); 2.77 (1H, t, J=2.5 Hz, 6-H); 3.34 (3H, s, 6-OMe); 3.54 (3H, s, OCH₂OMe); 5.25 and 5.34 (each 1H, each d, J=6 Hz, OCH₂OMe).

MS (C₂₉H₄₂O₅): Calc. 470.3032; Found 470.3033.

EXAMPLE 14

Synthesis of (22R,23R,25S)-6β-methoxy-23-methoxymethoxy-3α,5-cyclo-5α-24-norcholestano-26,22-lactone [compound (27)]

500 mg (1.06 mmol) of the compound (25) obtained by the preparation described in the Example 13 was dissolved in AcOEt, 300 mg of 5% Rh-Al₂O₃ was added thereto, and the mixture was shaken for 13 hours in the H₂ gas atmosphere of 7 atm. After the reaction liquid was filtered, the solvent was distilled from the filtrate, whereby 464 mg (yield 92%) of the compound (27) was obtained as a colorless amorphous solid.

$[\beta]_D$ +36.31° (C=1.03, CHCl₃)
IR $\nu_{max}^{CHCl_3}$ (cm⁻¹): 1770
¹HNMR (400 MHz) δ: 0.76 (3H, s, 18-H₃); 1.02 (3H, s, 19-H₃); 1.14 (3H, d, J=7 Hz, 21-H₃ or 27H₃); 1.24 (3H, d, J=7 Hz, 21-H₃ or 27H₃); 1.14 (3H, d, J=7 Hz, 21-H₃ or 27H₃); 2.70 (1H, m, 25-H); 2.78 (1H, t, J=2.3 Hz, 6-H); 3.33 (3H, s, 6-OMe); 3.42 (3H, s, OCH₂OMe); 4.31 (1H, dd, J=8.4 Hz, 23-H); 4.38 (1H, dd, J=4 Hz, 1.5 Hz, 22-H); 4.62 and 4.68 (each 1H, each d, J=7 Hz, OCH₂OCH₃).

MS (C₂₉H₄₆O₃): Calc. 474.3368; Found 474.3345.

The compound (27) prepared in the above-mentioned Example 11 can be transformed to bisnorbrassinolide as same case as in the synthesis of brassinolide from the aforementioned compound (6), of which reaction process is as described below with which detail will be described later as Reference.

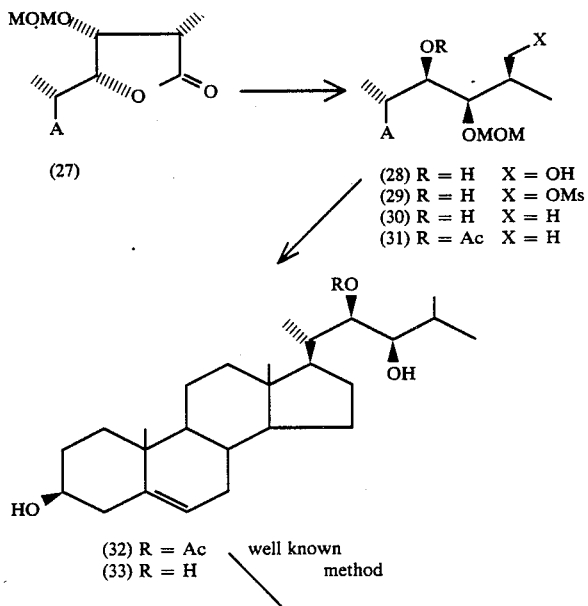

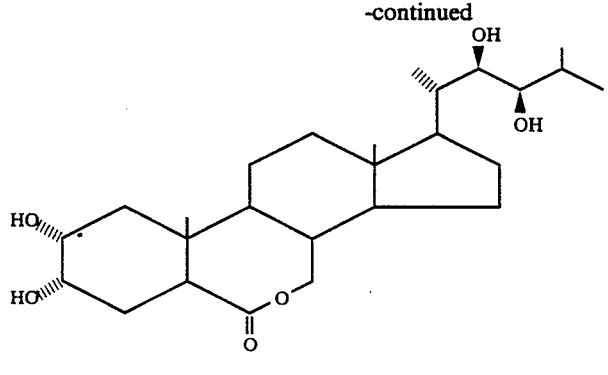

bisnorbrassinolide

Reference 5

Synthesis of bisnorbrassinolide from compound (27)

(i) Preparation of (22R,23R,25R)-22,26-dihydroxy-23-methoxymethoxy-6β-methoxy-3α,5-cyclo-24-norcholestane [compound (28)]

300 mg (0.63 mmol) of compound (27) was dissolved in 20 ml of THF, 72 mg (1.9 mmol) of LiAlH₄ was added thereto, and the obtained mixture was stirred for 20 min. at room temperature. 25% NaOH aq. solution was added to the reaction liquid, and the mixture was extracted with AcOEt, the extract was washed with saturated NaCl solution, and dried with Na₂SO₄. The solvent was distilled thereafter, whereby 300 mg (yield 99%) of compound (28) was obtained as a colorless amorphous solid.

IR $\nu_{max}^{CHCl_3}$ (cm⁻¹): 3400

¹NMR (400 MHz) δ: 0.72 (3H, s, 18-H₃); 0.90 (3H, d, J=7 Hz, 21-H₃ or 27-H₃); 1.02 (3H, s, 19-H₃); 1.12 (3H, d, J=7 Hz, 21-H₃ or 27-H₃); 2.78 (1H, t, J=2.3 Hz, 6-H); 3.33 (3H, s, 6-OMe); 3.45 (3H, s, OCH₂OMe); 3.56–3.78 (4H, m, 22-H, 23-H and 26-H₂); 4.66 and $\overline{4.81}$ (each 1H, each d, J=7 Hz, OCH₂OMe).

MS m/z: 463 (M⁺ − 15)

(ii) Preparation of (22R,23R,25S)-22-acetoxy-6β-methoxy-23-methoxymethoxy-3α,5-cyclo-5α-24-norcholestane [compound (31)]

300 mg (0.63 mmol) of compound (28) and 0.094 ml (0.67 mmol) of Et₃N were dissolved in 10 ml of CH₂Cl₂, and 0.052 ml (0.67 mmol) of MsCl was added thereto while cooling with ice. The mixture was stirred for 10 minutes at the temperature of 0° C., and a saturated NaHCO₃ aq. solution was added thereto. The mixture was extracted with AcOEt. After the extract was washed with saturated NaCl solution, it was dried with Na₂SO₄ and the solvent was distilled therefrom.

The obtained compound (29) was then dissolved in Et₂O (15 ml), 116 mg (3.14 mmol) of LiAlH₄ was added thereto, and the obtained mixture was stirred for 30 minutes at room temperature. The aq. solution of 25% NaOH was then added to the reaction liquid, which was extracted with AcOEt.

The extract was then washed with saturated NaCl solution, dried with Na₂SO₄ and the solvent was distilled therefrom, whereby 243 mg of the compound (30) was obtained.

Furthermore, the compound (30) was dissolved in the mixture of Ac₂O (1 ml)-pyridine (5 ml), 4-(N,N-dimethylamino)pyridine of catalytic amount was added thereto, and the mixture was stirred for 10 hours at room temperature. The reaction liquid was poured into water and extracted with AcOEt, and the extract was then washed with saturated NaCl solution, and dried with Na₂SO₄. The solvent was distilled thereafter. As a result of a treatment of the residue with silica gel column-chromatography, 260 mg of the compound (30) was obtained from an elution part of CH₂Cl₂-CHCl₃ (3:1 v/v) as an amorphous solid having a color of yellow tint.

[α]_D + 32.19° (c=1.26, CHCl₃)

IR $\nu_{max}^{CHCl_3}$ (cm⁻¹): 1730

¹HNMR (400 MHz) δ: 0.73 (3H, s, 18-H₃); 0.94 (3H, d, J=7 Hz, CH₃); 0.96 (3H, d, J=7 Hz, CH₃); 1.01 (3H, d, J=Hz, CH₃); 1.02 (3H, s, 19-H₃); 2.07 (3H, s, COCH₃); 2.76 (1H, t, J=2.3 Hz, 6-H); 3.32 (3H, s, 6-OMe); 3.37 (3H, s, OCH₂OMe); 3.85 (1H, t, J−9 Hz, 23-H); 4.55 and 4.68 (each 1H, each d J=7 Hz, OCH₂OME); 5.13 (1H, d, J=9 Hz, 22-H).

MS (C₃₁H₅₂O₅): Calc. 504.3828; Found 504.3815.

(iii) Preparation of (22R,23R)-3β,22,23-trihydroxy-24-norcholest-5-ene [compound (33)]

130 mg (0.26 mmol) of the compound (31) was dissolved in dioxane (4 ml)-H₂O (0.6 ml) mixture, TsOH (13 mg) was added thereto, and the mixture was heated for one hour at the temperature of 80° C. AcOEt (20 ml) was added to the reaction liquid which was washed with saturated NaHCO₃ aq. solution and saturated NaCl solution thereafter. The reaction liquid was then dried with Na₂SO₄ and the solvent was distilled therefrom.

100 mg of the obtained compound (32) was dissolved in 5% KOH-MeOH (4 ml), heated for one hour while refluxing.

30 ml of AcOEt was then added to the reaction liquid, which was washed with saturated NaCl solution thereafter. The reaction liquid was dried with Na₂SO₄ and the solvent was distilled therefrom.

The obtained raw crystal was recrystallized from MeOH-AcOEt, whereby 73 mg (yield 84%) of colorless crystal having mp 218°–220° C. (data on the literature: 219°–221° C.) was obtained.

Various spectral data of this product were accorded with the data described in the literature (Phytochemistry, 1984, 23, 525).

(iv) Preparation of 26,27-bisnorbrassinolide

The transformation from the compound (33) to bisnorbrassinolide was carried out in accordance with the method described in the J. Ame. Chem. Soc. 102, 6580 (1980).

γ-lactone derivatives of the present invention can be easily transformed after reduction by the well-known method, so as to produce brassinolide, epibrassinolide or bisnorbrassinolide, and accordingly they are most important starting material for the synthesis of brassinolide derivative or epinorbrassinolide derivative.

What is claimed is:

1. Gamma-lactone derivatives represented by the formula (I)

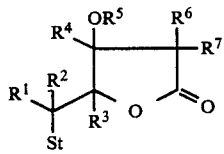

wherein

R$^1$ is methyl group or is combined with R$^2$ to form a methylene group;

R$^2$ is hydrogen, a hydroxyl group or a trifluoroacetoxyl group, or is combined with R$^1$ as above recited, or is combined with R$^3$ to form a pi bond;

R$^3$ is hydrogen or is combined with R$^2$ as above recited; R$^4$ and R$^6$ are each hydrogen, or are combined to form a pi bond;

R$^5$ is hydrogen or a protecting group for a hydroxyl group;

R$^7$ is hydrogen or a straight-chain or a branched alkyl group; and

St is a steroid nucleus represented by the following formula (B):

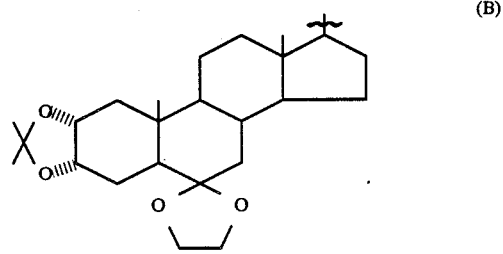

2. Gamma-lactone derivatives claimed in the claim 1 wherein the gamma-lactone derivative is (2R, 3S,20R,22R)-6,6-ethylenedioxy-20-hydroxy-2,3-isopropylidenedioxy-23-methoxymethoxy-5α-ergost-23-eno-28,22-lactone.

3. Gamma-lactone derivatives claimed in the claim 1 wherein the gamma-lactone derivative is (2R, 3S,20Z)-6,6-ethylenedioxy-2,3-isopropylidenedioxy-23-methoxymethoxy-5α-ergost-20(22),23-diene-28,22-lactone.

4. Gamma-lactone derivative claimed in the claim 1 wherein the gamma-lactone derivative is (2R, 3S,22R,23R,24S)-6-,6-ethylenedioxy-2,3-isopropylidenedioxy-23-methoxymethoxy-5α-ergostano-28,22-lactone.

* * * * *

UNITED STATES PATENT AND TRADEMARK OFFICE
CERTIFICATE OF CORRECTION

PATENT NO. : 4,939,247
DATED : July 3, 1990
INVENTOR(S) : Kametani, et al

It is certified that error appears in the above-indentified patent and that said Letters Patent is hereby corrected as shown below:

Title page, item [57],
  Abstract, that portion of formula (B) which reads

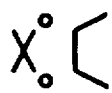  should read  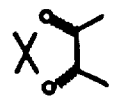

Column 3, lines 3 - 8, that portion of formula (III) which reads

  should read  

Column 3, lines 18 - 25, that portion of formula (I) which reads

  should read  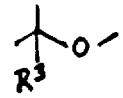

UNITED STATES PATENT AND TRADEMARK OFFICE
CERTIFICATE OF CORRECTION

PATENT NO. : 4,939,247
DATED : July 3, 1990
INVENTOR(S) : Kametani, et al

It is certified that error appears in the above-indentified patent and that said Letters Patent is hereby corrected as shown below:

Column 3, lines 36 - 45, that portion of formula (19) which reads

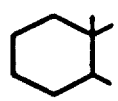   should read   

Column 7, that portion of formula (14) which reads

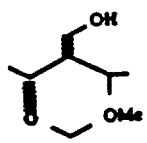   should read   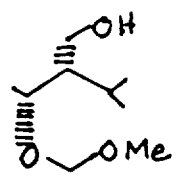

Column 7, that portion of formula (15) which reads

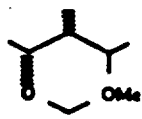   should read   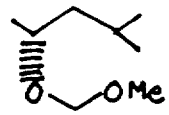

UNITED STATES PATENT AND TRADEMARK OFFICE
CERTIFICATE OF CORRECTION

PATENT NO. : 4,939,247
DATED : July 3, 1990
INVENTOR(S) : Kametani, et al

It is certified that error appears in the above-indentified patent and that said Letters Patent is hereby corrected as shown below:

Column 7, that portion of formula (17) which reads

  should read  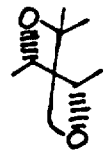

Column 9, that portion of formula (19) which reads

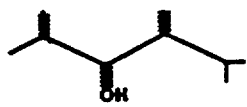  should read  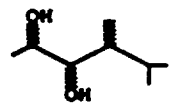

UNITED STATES PATENT AND TRADEMARK OFFICE
CERTIFICATE OF CORRECTION

PATENT NO. : 4,939,247
DATED : July 3, 1990
INVENTOR(S) : Kametani, et al

It is certified that error appears in the above-indentified patent and that said Letters Patent is hereby corrected as shown below:

Column 13, the formula which reads

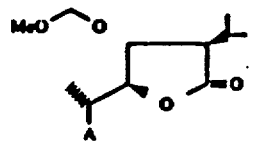   should read   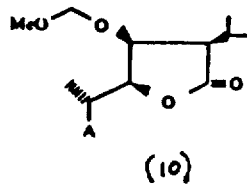

Signed and Sealed this

Fifteenth Day of March, 1994

Attest:

BRUCE LEHMAN

Attesting Officer    Commissioner of Patents and Trademarks